United States Patent
Birchak et al.

(10) Patent No.: US 6,354,146 B1
(45) Date of Patent: Mar. 12, 2002

(54) ACOUSTIC TRANSDUCER SYSTEM FOR MONITORING WELL PRODUCTION

(75) Inventors: James Robert Birchak, Spring; Robert Anthony Moore, Katy; Eugene J. Linyaev, Houston; John Preston Rogers, Richmond, all of TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 09/334,830

(22) Filed: Jun. 17, 1999

(51) Int. Cl.⁷ .......................... G01N 29/00; E21B 43/17
(52) U.S. Cl. ...................... 73/61.79; 166/308
(58) Field of Search ........................ 73/61.79, 861.28, 73/861.08, 861.02, 152.49, 152.32; 340/853.3, 854.9; 166/308, 250.09, 250.17

(56) References Cited

U.S. PATENT DOCUMENTS

| | | | |
|---|---|---|---|
| 3,891,871 A | * 6/1975 | Henriquez et al. | 310/337 |
| 4,255,798 A | 3/1981 | Havira | 367/35 |
| 4,432,077 A | * 2/1984 | Alhilali et al. | 367/31 |
| 4,601,024 A | 7/1986 | Broding | 367/86 |
| 4,787,252 A | * 11/1988 | Jacobson et al. | 73/861.28 |
| 4,805,156 A | 2/1989 | Attali et al. | 367/35 |
| 4,916,648 A | 4/1990 | Gard | 367/35 |
| 4,999,817 A | 3/1991 | Zimmer | 367/69 |
| 5,001,676 A | 3/1991 | Broding | 367/31 |
| 5,033,032 A | * 7/1991 | Houghtaling | 367/160 |
| 5,216,638 A | 6/1993 | Wright | 367/35 |
| 5,270,985 A | * 12/1993 | Thomas et al. | 367/142 |
| 5,367,911 A | * 11/1994 | Jewell et al. | 73/861.08 |
| 5,477,101 A | 12/1995 | Ounadjela | 310/334 |
| 5,594,176 A | 1/1997 | Kiefer | 73/623 |
| 5,652,617 A | 7/1997 | Barbour | 348/85 |
| 5,841,734 A | 11/1998 | Ritter et al. | 367/35 |

FOREIGN PATENT DOCUMENTS

| | | | |
|---|---|---|---|
| EP | 054941 9 A2 | 6/1993 | G01V/1/40 |
| GB | 2066466 | * 7/1981 | G01P/5/00 |
| SU | 504163 | * 7/1974 | G01V/1/40 |

\* cited by examiner

Primary Examiner—Hezron Williams
Assistant Examiner—Jay L. Poulitzer
(74) Attorney, Agent, or Firm—Conley, Rose & Tayon P.C.

(57) ABSTRACT

A method and apparatus for measuring properties of fluid flowing through a bore, using a signal transmitted substantially perpendicularly to the direction of flow. A preferred embodiment uses a pair of acoustic transducers mounted in the annular body of the fluid conduit. The tool is constructed so as to be able to operate for a period of years in a downhole environment without maintenance or replacement. An transducer is also described that is adapted to fit within the dimensions of an annular body without suffering a reduction in the length of the transducer backing.

21 Claims, 7 Drawing Sheets

ACOUSTIC TRANSDUCER SYSTEM FOR MONITORING WELL PRODUCTION

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD OF THE INVENTION

The invention relates generally to apparatus and methods for acoustically determining various properties of a fluid flowing through a conduit. More particularly, the present invention relates to an acoustic transducer system for monitoring production fluids in completed wells. Still more particularly, the present invention comprises a tool having one or more opposed transducer pairs that are acoustically isolated from the tool body and transmit acoustic signals across the fluid stream. Applications of the present invention also include an angled transducer backing that allows transducers to be used in any annular device, including tubing and rotating logging heads. Transducers configured in accordance with the present invention can be used in either pitch-catch or pulse-echo mode.

BACKGROUND OF THE INVENTION

Description of the Related Art

Production of hydrocarbons from geologic formations in the earth is typically accomplished by drilling a well to the desired formation. Once the desired drilling objectives have been met and prior to the start of production, the well undergoes a completion process. The completion process entails cementing the annulus between the casing and the borehole wall and isolating the production zone(s) from the rest of the strata. The casing is perforated at the production zone(s) so as to allow the formation fluids to drain into the casing. To isolate the production zones from other fluids in the casing, production tubing is installed inside the casing. The formation fluids, comprising mainly gaseous or liquid hydrocarbons, flow upward through the production tubing to the surface, where they are captured for processing.

Once a well has been completed in this manner, it may produce steadily and require no further attention for many years. Nevertheless, for a variety of reasons, it may be desirable to monitor the flow of fluids through the production tubing, using sensors installed in sensor modules that are deployed as part of the production tubing string. For example, the controlling equipment that receives the fluids from the formation may need to be modified or optimized, depending on the nature of the fluids it receives. Similarly, it may be desirable to monitor each producing zone in order to detect the encroachment of water, gas, or other undesired fluid into the well. It is often necessary to maintain data on the rate at which each of the flowstream constituents is produced for one or more wells in a reservoir in order to monitor the effectiveness of a reservoir production scheme, detect faults in the production equipment for an individual well, and/or in determine royalty payments for produced hydrocarbons. Hence, the pressure, temperature, flow rate, density, chemical composition and water content are all properties of the fluid stream whose measurement would be advantageous.

Because many wells are remote and/or offshore, it is often desirable to install equipment that allows unmanned or automatic mode monitoring of the producing well. For example, it is desirable to provide a production monitoring system that can measure the desired parameters and transmit the resulting data to a remote data-receiving site.

Similarly, because the monitoring system is downhole, maintenance or replacement of the monitoring system requires a trip into the hole and a corresponding interruption in production, Hence, it is desirable to maximize the period for which a production system can operate without maintenance or replacement. An ideal production monitoring system would be able to operate for at least twenty and up to thirty or more years without interruption, so as to reduce the amount of downtime and maximize efficiency. The corrosive environment that exists downhole reduces the types of equipment that are suitable for this application.

In addition, it is further desirable to minimize the amount of flow disruption caused by the monitoring sensors or tool. This typically means that the configuration of the sensors must correspond to the inside diameter of the production tubing. Hence, it is further desired to provide an effective production monitoring tool that can fit within the dimensions of the production tubing itself.

Finally, it is important that the monitoring system be capable of assessing a wide range of fluids. Production from most oil wells takes the form of a multicomponent fluid stream. For a typical oil well this stream may include crude oil, brine, hydrocarbon gases, various inorganic gases, and minor amounts of particulate matter. The proportion of each constituent of the production flowstream varies from well to well, and in a single well can vary significantly over time.

Various systems currently exist that purport to meet these requirements. Early methods for determining the fractional representation of the various fluids, i.e. liquids, gases, and combinations thereof, within the flowstream of an oil well relied on manual sampling and analytical procedures. A representative sample of the flowstream was collected and through physical separation and chemical analysis the fractional representation of each constituent was determined. Manual analysis is still used today in many instances, particularly where accuracy is particularly important. However, manual testing is relatively expensive, especially in remote oil fields or where frequent updating is necessary. Further, collecting small volume samples that accurately represent the flowstream is difficult, especially in high pressure, high temperature production systems.

Automated flowstream analysis systems have been developed to avoid much of the expense associated with manual testing. Early automated systems relied on gravity driven physical separation of the constituents of the flowstream. Such systems are not accurate for applications where the flowstream includes an oil-water emulsion, which cannot be gravity separated. Such systems are also of limited use for heavy oil reservoirs, where the density difference between the produced oil and brine is too small to provide significant driving force for gravity separation. Gravity driven automated analysis systems also tend to be bulky, expensive, and require careful maintenance.

Many additional, alternative techniques have been proposed to measure flow characteristics of fluids contained in tubular conduits. For example, some known techniques are based on sensing and correlating local pressure fluctuations or sensing the pressure field set up by a venturi or vortex element. Other techniques use measurements of the effect of the fluid stream on various types of radiation, such as gamma rays, to determine fluid properties. These techniques have obvious disadvantages, including safety and the continuous decay of the radiation source.

Acoustic monitoring systems use ultrasonic transducers that, through known acoustic signaling and signal processing techniques, are able to derive information about the fluid stream. Specifically, the speed of sound for a fluid can be calculated using the known distance between a transmitting transducer and a receiving transducer and the measured time required for a signal to traverse that distance. The transducers are typically annular rings that are spaced apart along the axis of the tool. Acoustic signals are transmitted axially, parallel to the direction of the fluid flow. An example of such a device is described in U.S. Pat. No. 4,003,252 to Dewath. The apparatus disclosed in the Dewath patent uses transducers recessed in the acoustically damping liner of a tube.

None of the prior art devices have been entirely satisfactory, however. Many of the conventional multiphase flow metering systems do not provide an accurate indication of the flow velocity of when the fluid flow is multiphase. Other conventional systems are prohibitively difficult to install or incorporate intrusive metering arrangements requiring interruption or alteration of the flow. Many conventional systems are compatible with only a limited range of pipeline designs and, accordingly, have limited utility. Finally, many systems are not capable of extended operation in the corrosive downhole environment.

SUMMARY OF THE INVENTION

One object of the present invention is to provide an acoustic fluid stream monitoring system that can be positioned within an annular shell. Another object of the present invention is to provide a means for measuring the flow of multicomponent streams, including streams comprising both gas and liquid, through a pipe. Still another object of the invention is to provide a tool that is capable of withstanding the downhole environment for at least twenty years.

The present invention comprises a novel acoustic transducer configuration that can be mounted in an annular shell having the same dimensions as the tubing that transmits the fluid stream. In a preferred embodiment, at least two transducers are positioned on opposite sides of the annular shell, with their operative faces directed into the center bore of the shell. Preferably, the transducers face each other across the bore. In another preferred embodiment, transducers are positioned with their operative faces directed out toward the formation.

The present invention further comprises a novel transducer configuration that allows a transducer having a relatively long backing to fit into the reduced space available in an annular volume without severely compromising the signal amplitude available from that transducer. In the novel transducer configuration, the transducer face has an orientation that is normal or substantially normal to a radius of the tubing, but the backing that extends behind the transducer face is angled relative to both the transducer face and the head radius, so that its length is not limited by the available annular thickness.

BRIEF DESCRIPTION OF THE DRAWINGS

For a more detailed description of the present invention, reference will now be made to the accompanying Figures, wherein.

DETAILED DESCRIPTION OF THE INVENTION

Figure 1:
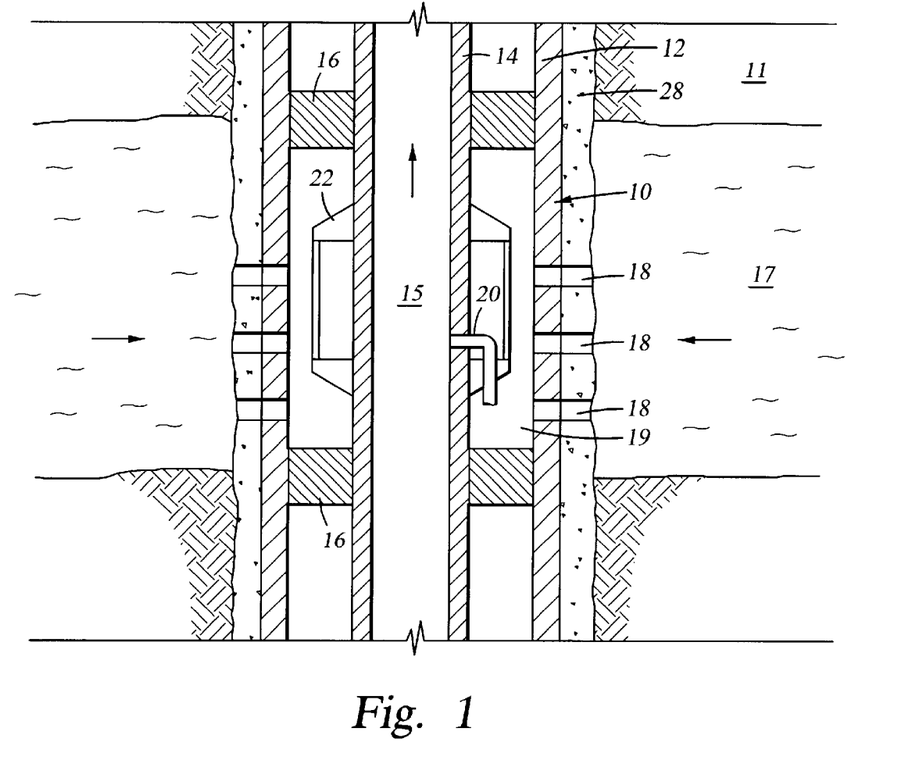
FIG. 1 is a schematic representation of a fluid monitoring system constructed in accordance with the principles of the present invention and in place in a competed well.

Referring initially to FIG. 1, a completed well 10 in a formation 11 typically includes a casing 12 and production tubing 14. Cement 28 fills the annulus between casing 12 and formation 11. One or more packers 16 are used to isolate zones along the well axis from one another. At one or more producing zones 17, the casing is perforated as at 18 so as to allow the ingress of formation fluids. A passage 20, preferably valved, allows the fluid to enter production 14 tubing from the annulus 19 between casing 12 and production tubing 14. Passage 20 can pass through sensor sub 22 as shown, or can be remote (not shown). If remote, fluid entering passage 20 must be monitored by the controlling sub sensors. The fluids then flow up to the surface through the bore 15 of production tubing 14.

Sensor Sub

Figure 2:
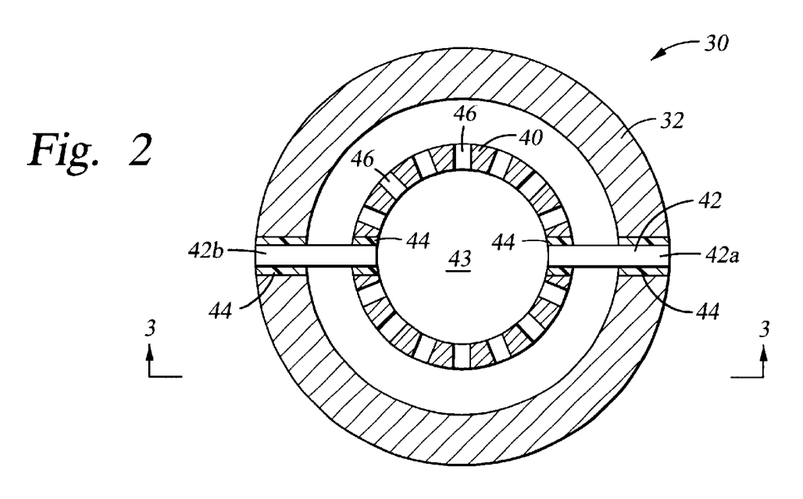
FIG. 2 is a cross-sectional end view of a sensor sub constructed in accordance with the principles of the present invention.
Figure 3:
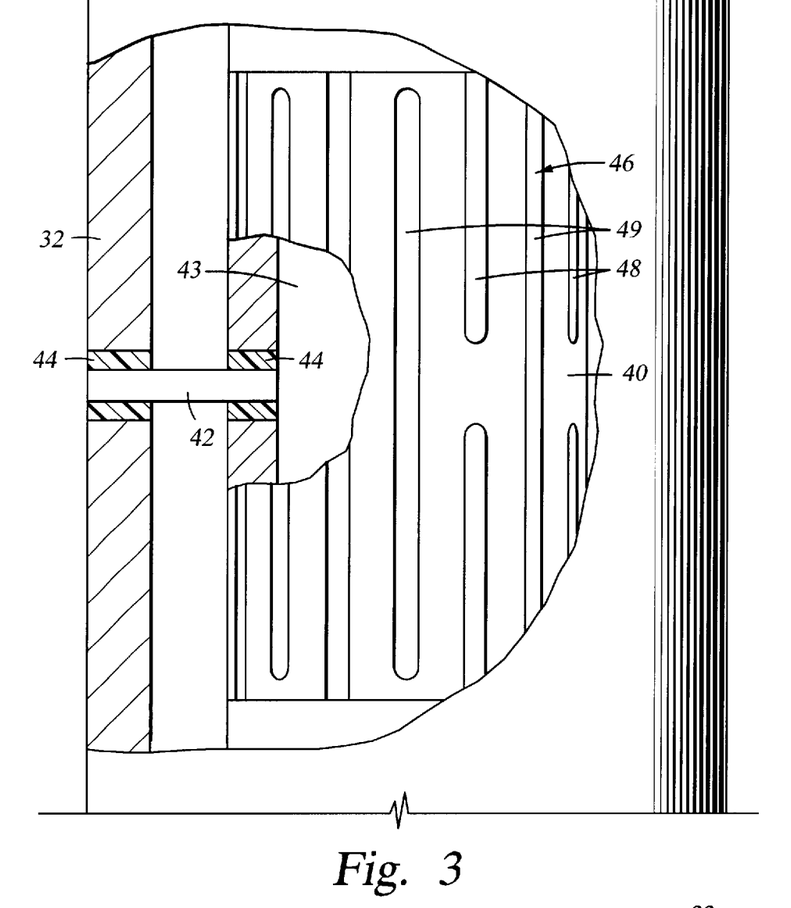
FIG. 3 is a partially cut away side view taken along lines 3—3 of FIG. 2.

The sensors of the present monitoring tool are preferably located in a sensor sub 22 that forms part of the production tubing 14 at or above the entry point for the fluids that are to be monitored. Referring now to FIGS. 2 and 3, a first, preferred embodiment of an acoustic monitoring system 30 comprises an outer shell 32 and an inner shell 40. Outer shell 32 is preferably adapted to support the mechanical load applied to the production string and is therefore substantially solid. Inner shell 40 has a central bore 43 through which production fluid passes on its way to the surface. Inner shell 40 is preferably adapted to support one or more pairs of transducer assemblies 42a, 42b, described in detail below. One of transducer assemblies 42a,b is a transmitter adapted to provide an acoustic signal to the fluid in bore 43 and the other is adapted to receive the acoustic signal from the fluid. Because an acoustic signal is transmitted more quickly and efficiently by solid metal than by a fluid, however, the portion of the acoustic signal transmitted circumferentially from transducer assembly 42a to transducer assembly 42b along a path through the metal body of inner shell 40 will overshadow and obscure the portion of the signal that is transmitted through the fluid in bore 43 unless measures are taken to attenuate the former. According to one embodiment, these measures include the use of signal-damping bushings 44 that support transducer assemblies 42 in inner shell 40 and the placement of multiple longitudinal slots 46 in the body of inner shell 40. Bushings 44 are preferably made of epoxy potting or Teflon®. Slots 46 preferably alternate between slots 48 that intersect the end of inner shell 40 and slots 49 that do not. When configured this way, slots 46 break up the circumferential path that would otherwise allow the acoustic signal to be transmitted efficiently from transducer assembly 42a to transducer assembly 42b through the body of inner shell 40. By configuring slots 46 as shown, the length of the path through the shell body is greatly increased, with a corresponding attenuation in the signal as it is transmitted along that path. In other instances, it may be acceptable to provide fewer slots, or slots that are differently configured, but in any event it is desirable to lengthen the path through the tool body sufficiently to prevent it from interfering with the signal travelling along the desired path.

It is preferred but not required to fill slots 46 with a signal damping material, such as epoxy potting or Teflon®. The length and number of slots 46 can be adjusted to ensure that the portion of the signal transmitted through inner shell 40 is sufficiently attenuated. Outer shell 30 does not include signal attenuating slots because this would tend to weaken outer shell 30, whose purpose is to provide mechanical support. Nevertheless, the portion of the acoustic signal that is transmitted circumferentially through outer shell 30 is insignificant, because transducers 42 are acoustically isolated from outer shell 30, preferably by signal-damping bushings made of epoxy potting or Teflon®.

While transducer assemblies 42 are shown extending radially outward through outer shell 30, this is not necessarily the case. Transducer assemblies 42 can be any desired length, so long as they fit within the dimensions of the sensor sub and so long as their backings are long enough to adequately attenuate the backing reverberations that are generated when each transducer is fired.

Figure 4:
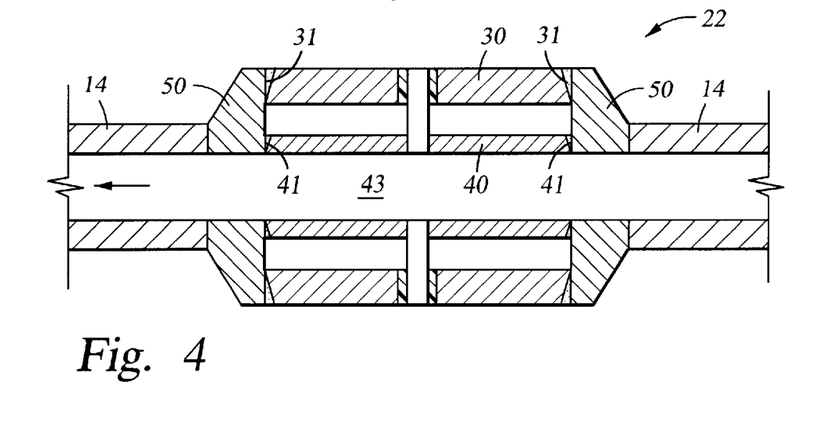
FIG. 4 is a longitudinal cross-section of the sensor sub shown in FIG. 2.

Referring now briefly to FIG. 4, the sensor sub 22 may have an outside diameter that is greater than the outside diameter of production tubing 14. For example, outer shell 30 and inner shell 40 can be connected to production tubing 14 by a pair of end pieces 50 that provide a transition from the outside diameter of production tubing 14 to the outside diameter of outer shell 30. End pieces 50 are preferably welded to the ends of outer shell 30 and inner shell 40 at welds 31, 41, respectively. End pieces 50 should be at sufficient distance from the transducers so that acoustic arrivals from the end pieces cannot interfere with the fluid measurements. An example of a suitable distance is ten times the fluid path length.

Figure 5A:
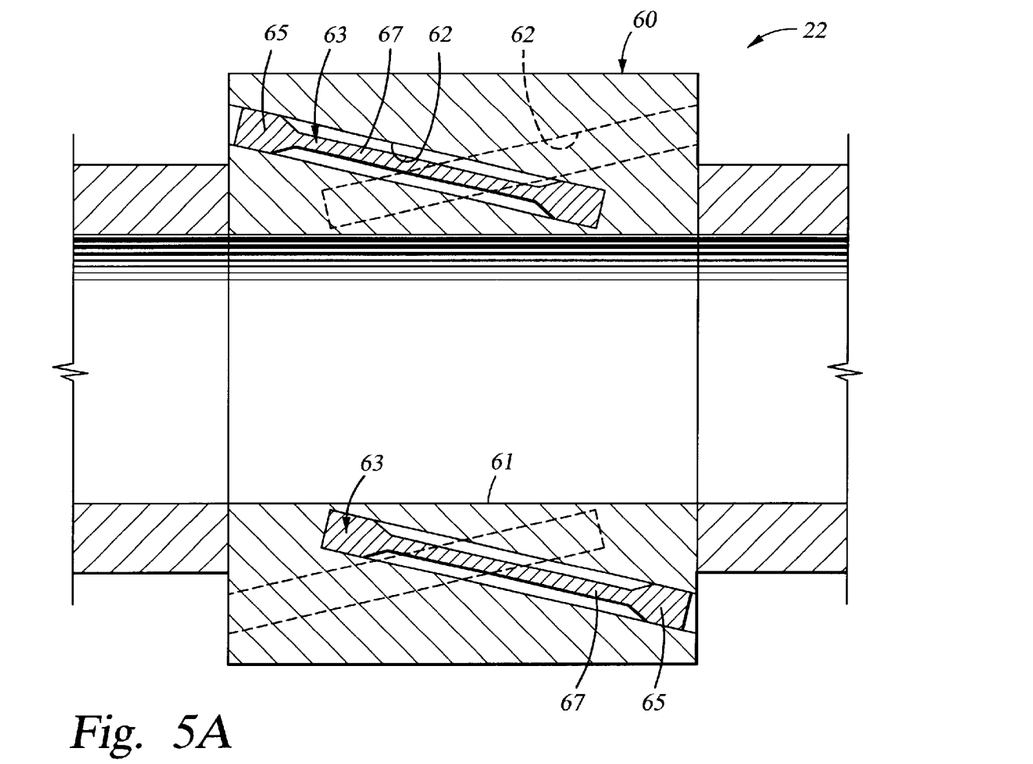
FIGS. 5A–B are longitudinal and normal cross-sectional views of a first alternative embodiment of the present sensor sub.
Figure 5B:
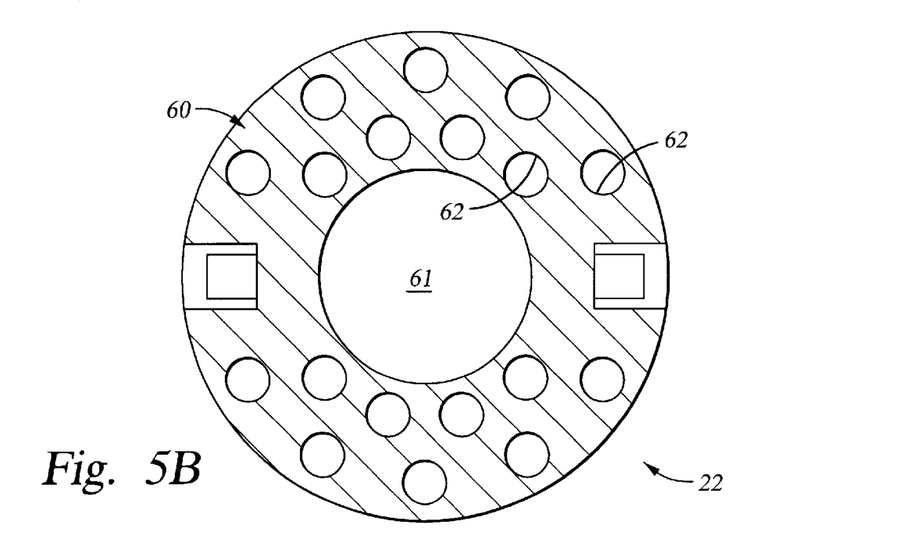

Referring now to FIGS. 5A and 5B, an alternative embodiment for sensor sub 22 is shown in cross-section. According to this embodiment, the housing is a single annular shell 60 having a central bore 61 and a plurality of generally longitudinal bores 62 extending therethrough. Shell 60 preferably has an outer diameter that is significantly larger than the outer diameter of the adjacent pipe. Bores 62 are preferably slightly inclined with respect to the tool axis, as shown. Each bore 62 defines a cavity within which is preferably positioned a signal damping slug 63. Each slug 63 preferably includes at least one end portion 65 having a diameter substantially equal to the inside diameter of the bore 62 in which it is received. In this manner slug 63 provides support for the bore 62 and helps reduce the risk that bore 62 will be crushed. Each slug 63 preferably also includes a neck portion 67 having a diameter that is smaller than the inside diameter of the bore. This creates an annular space around neck 67, which helps prevent the acoustical transmission. In some embodiments, an acoustical attenuation fluid may be provided in the gap. Suitable acoustical signal attenuators are also fully described in U.S. Pat. No. 5,510,582, which is incorporated herein in its entirety. Alternatively, bores 62 are preferably filled with a signal-damping material such as tungsten loaded rubber. Bores 62 are preferably provided in sufficient number and in such spacing as to attenuate the portion of the acoustic signal that is transmitted circumferentially through shell 60 enough to prevent it from obscuring the portion of the signal transmitted through the fluid in central bore 61. In this embodiment, shell 60 supports both transducers 42 and the mechanical load applied to the production string.

Figure 6:
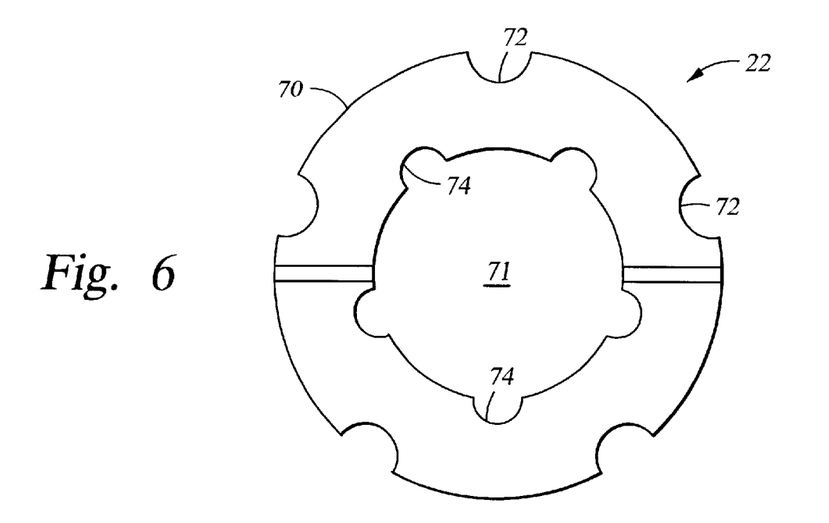
FIG. 6 is a cross-sectional end view of a second alternative embodiment of the present sensor sub.

As shown in FIG. 6, another alternative embodiment for sensor sub 22 comprises a sub body 70 having a central bore 71 therethrough. In this embodiment, the path of the circumferential tool body signal is lengthened by removing alternating segments of the tool body, as at 72, 74. The location and shape of the removed material must be designed to maintain sufficient mechanical strength to withstand tubing stresses that occur during operations and packer setting.

Transducers

Figure 7:
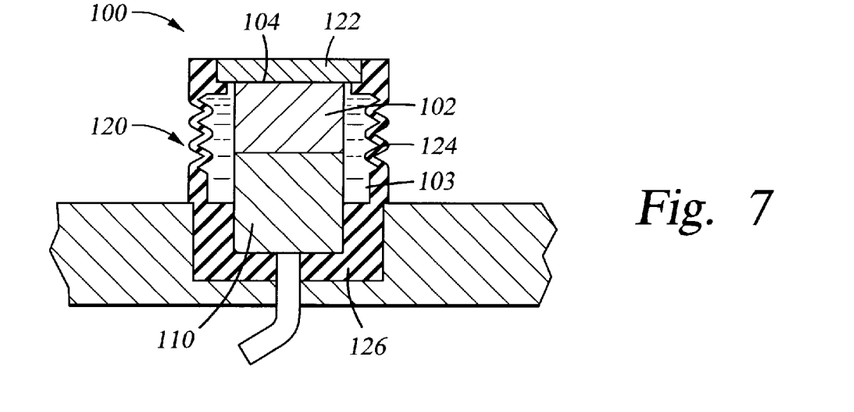
FIG. 7 is a schematic representation of a preferred embodiment of a novel transducer configuration according to the present invention.
Figure 7A:
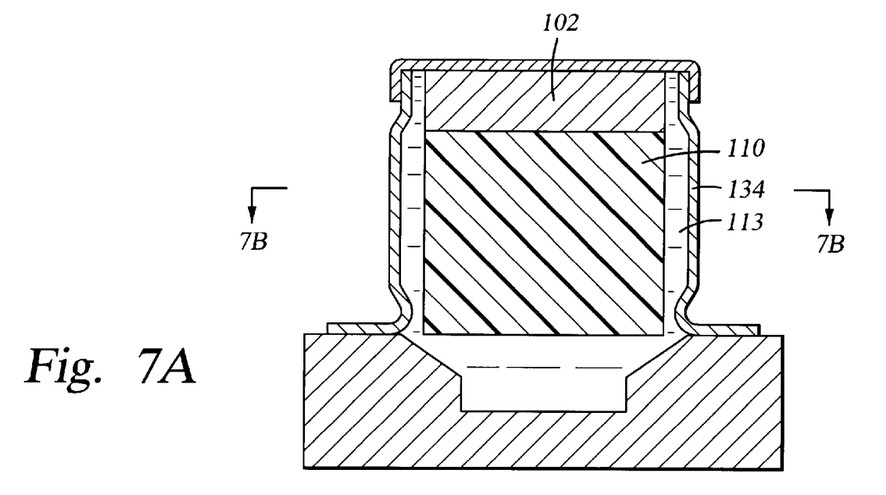
FIG. 7A is a schematic representation of an alternative embodiment of the present transducer.
Figure 7B:
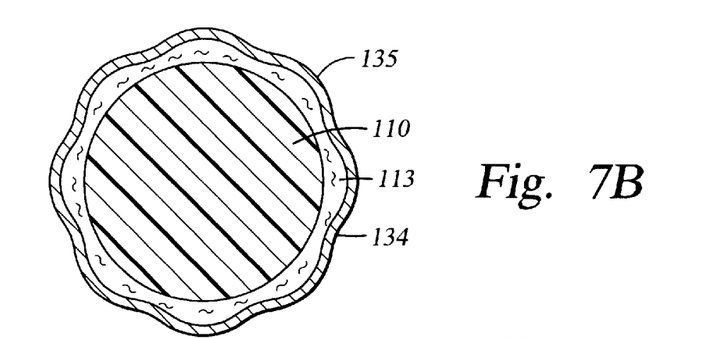
FIG. 7B is a cross-sectional view taken along the lines B—B of FIG. 7A.
Figure 7C:
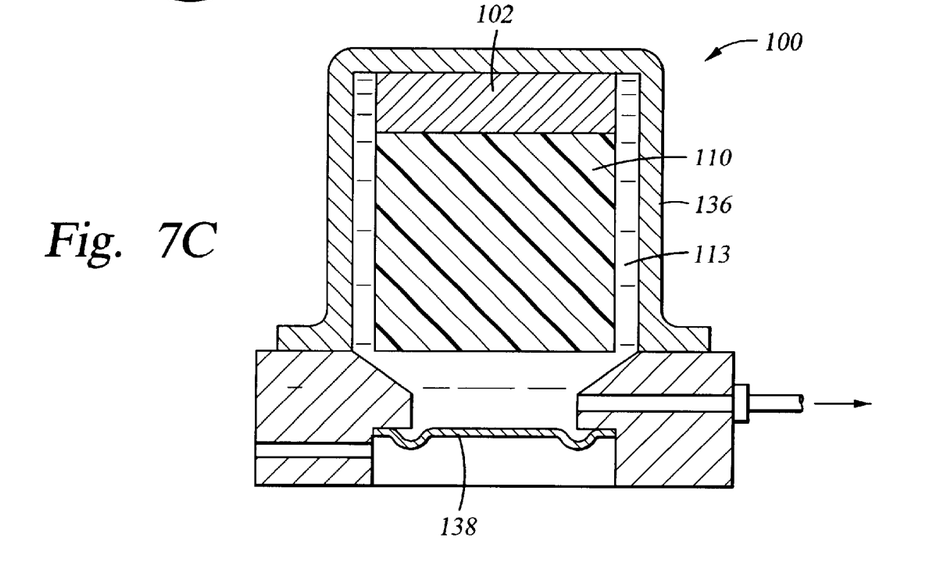
FIG. 7C is a schematic representation of a second alternative embodiment of the present transducer.

Referring now to FIG. 7, a preferred transducer 100 for use in the present invention includes a piezoelectric element 102 mounted on a backing member 110. Piezoelectric element 102 and backing member 110 are enclosed in a housing 120 that comprises an acoustical window 122, a flexible corrugated sleeve 124 and a rigid sealing base 126. The outer surface 104 of piezoelectric element 102 preferably contacts the inside of window 122. In one preferred embodiment, corrugated sleeve 124 acts as a spring that biases piezoelectric element 102 toward window 122. Housing 120 is preferably sized such that there is a small annular space 103 surrounding piezoelectric element 102 mounted and backing member 110. This volume is preferably filled with a liquid having good acoustical properties, such as silicone oil or Fluorinert®. The sealed configuration in which the backed piezoelectric transducers are supported in the tool preferably includes means for balancing hydrostatic pressure on the inside of the transducer housing with the hydrostatic pressure outside the transducer housing. Because the hydrostatic pressure of the fluid in the production tubing (i.e. outside the transducer housing) fluctuates with depth and in response to variations in pressure at the surface and variations in fluid weight, the volume of the fluid inside housing 120 needs to fluctuate so as to maintain a pressure balance. The pressure balance is needed if any component of the transducer, such as the backing, permanently deforms under pressure. In the present device, variations in fluid volume are achieved by flexing of corrugated sleeve 124. Fluctuations in hydrostatic pressure are matched by expansions or contractions of the fluid surrounding transducer 102 and corresponding movement of sleeve 124, thereby allowing hydrostatic pressure to remain equal inside and outside the housing. FIGS. 7A and 7C depict alternative embodiments of transducer housings that include pressure balancing systems. In particular, in FIG. 7A, transducer 102 is housed in a can 134, which includes a fluted wall 135 (FIG. 7B) that allows the volume within the can to fluctuate. As in FIG. 7, piezoelectric element 102 and backing member 110 are surrounded by a fluid 113, such as Fluorinert®. In FIG. 7C, the volume of can 136 is fixed and the volume of the fluid 113 surrounding piezoelectric element 102 and backing member 110 is allowed to vary through the flexing of a diaphragm 138. While one side of diaphragm 138 contains the fluid inside can 136, the other side of diaphragm 138 is in fluid communication with the borehole fluid. Still another alternative configuration for transducer 100 is shown and described in U.S. Pat. No. 5,644,186, which is incorporated herein in its entirety.

Figure 8:
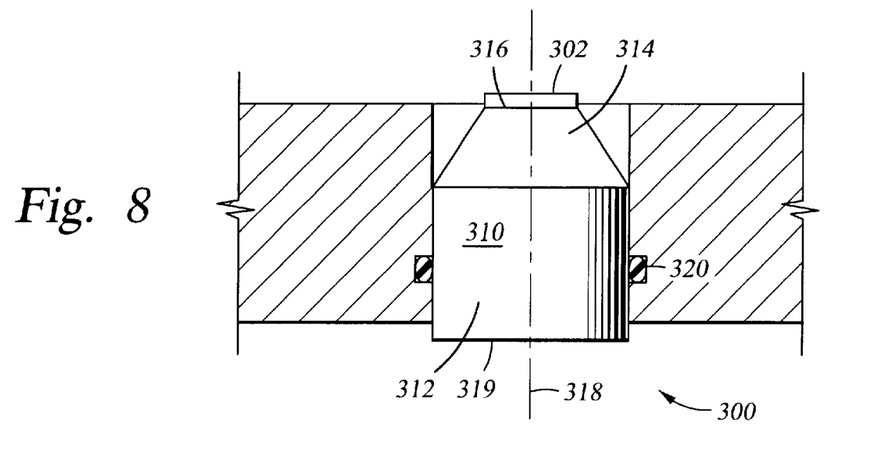
FIG. 8 is a schematic representations of a first alternative embodiment of a novel transducer configuration.

Referring now to FIG. 8, an alternative transducer 300 for use in the present invention includes a piezoelectric element 302 mounted on a backing member 310. Piezoelectric element 302 has an exposed surface and a backing surface and is preferably, but not necessarily, non-circular. Backing 310 preferably comprises a cylindrical base 312 and a tapered extension 314, which terminates at a face 316, which corresponds in shape to the shape of the backing surface of piezoelectric element 302. Piezoelectric element 302 is affixed to face 316 in a conventional manner. Backing 310 is mounted in a recess with piezoelectric element 302 oriented toward the fluid in the central tool bore and its innermost surface 319 preferably in fluid communication with a hydrostatic pressure balancing system. Tapered extension 314 may have any cross-section, but a conical or pyramid-shaped extension may be most advantageous due to manufacturing considerations. Regardless of the shape of extension 314, it preferably shares a common axis 318 with backing 310. It is further preferred, but not necessary that the transducer mount include an O-ring 320 that forms as seal between the tool body and backing 310. This seal prevents the oil or other fluid used in the fluid-pressure balancing system from leaking out around the transducer. It is also preferred that the surfaces of tapered backing extension 314 not touch the material from which the tool body is formed, so as to avoid undesired secondary reverberations. It will be understood by those skilled in the art that individual features of the foregoing system can be altered or substituted without altering the overall operation of the system.

Tomography

While the transducers in FIGS. 2–6 are shown as a single pair opposing each other along a diameter of the tool, it is contemplated that some instances it will be desirable to construct a tool where this is not the case. For example, it is necessary to provide multiple acoustic paths through the fluid when it is desired to characterize a multiphase, inhomogeneous fluid. Hence, in FIG. 9 a sensor sub 400 includes an array comprising four transmitter/receiver pairs. The first, 410a–b, oppose each other along a diameter 410c. Second and third pairs 412a–b and 413a–b oppose each other along chords, respectively 412c and 413c, that transect the central bore. Chords 412c and 413c may or may not be parallel to the diameter between 410a and 410b. Finally, a fourth pair, 414a–b, oppose each other along a line 414c that is preferably substantially perpendicular to 410c. The composite information received from these transducer pairs can be used in a sparse tomographic analysis to yield information about the number and relative proportion of phases present in the fluid stream. The tomographic information may include attenuation and speed of sound along each path. It will be understood that a tomographic array in accordance with the present invention may have more or fewer than four pairs of opposed transducers.

Figure 9:
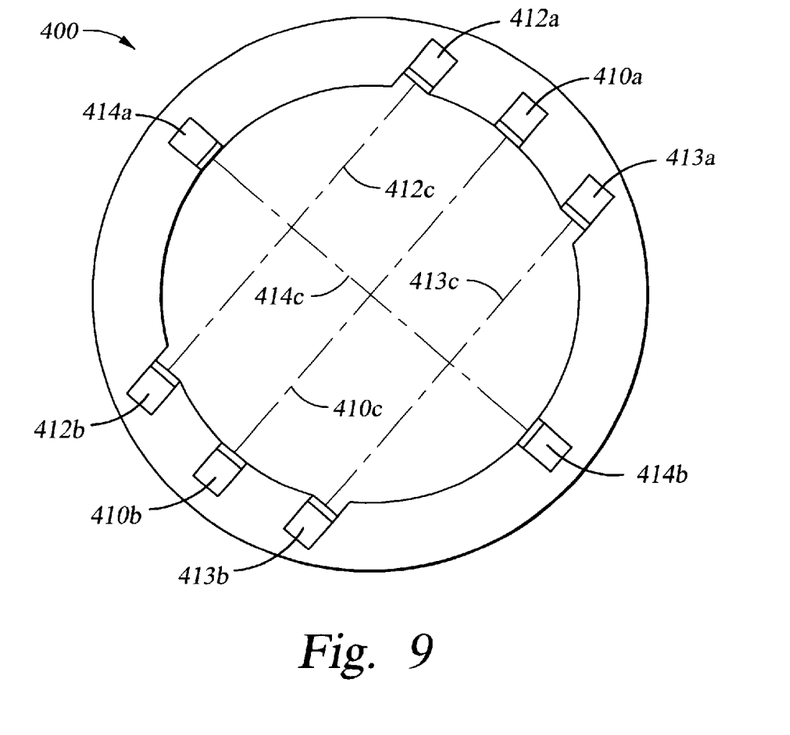
FIG. 9 is a schematic cross section showing four pairs of transducers configured so as to yield a plurality of signals that can be used in a tomographical analysis.
Figure 9A:
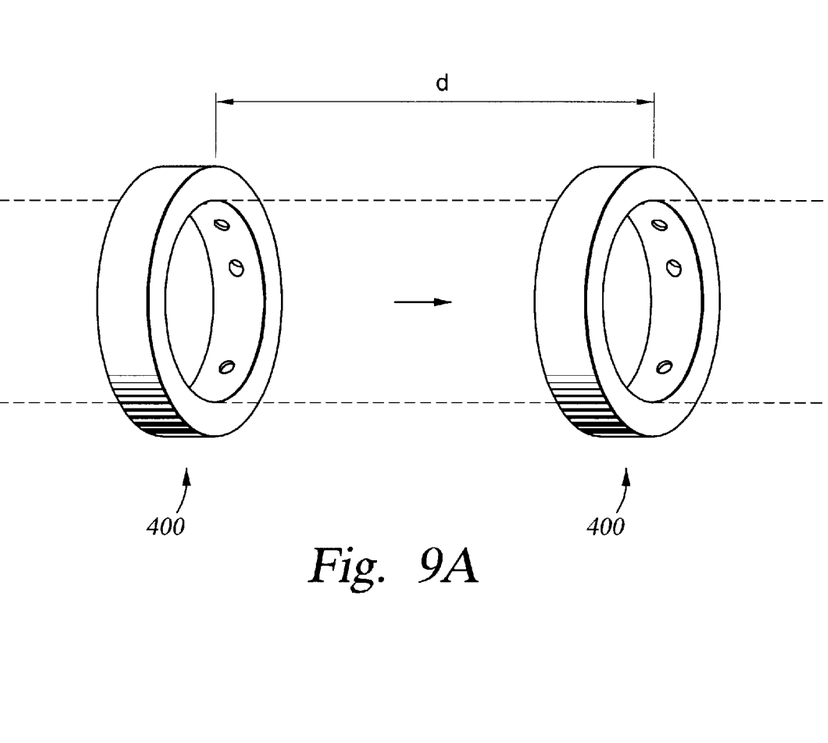
FIG. 9A is a schematic diagram showing a pair of multi-transducer rings axially spaced apart so as to permit correlation flow measurements for inhomogeneous fluids.

In addition, a correlation flow meter can be formed by using two rings of transducers like those shown in FIG. 9. As shown in FIG. 9A, two or more tomographic arrays 400 such as the one shown in FIG. 9 can be spaced apart a distance d along the longitudinal axis of the tool. For multiphase fluids, the correlation between patterns in the first ring and those in a second ring will have a time delay related to the movement of the pattern from one ring axially to the other. The flow velocity equals the axial distance between the rings divided by the time it takes for the pattern to move axially from one ring to the next. Hence, using cross correlation between arrays, in conjunction with pattern recognition, one can estimate the delay time $t_d$ for a pattern to travel the distance d. The flow velocity of the material contained in the inhomogeneity is equal to $v_f = d/t_d$.

Figure 10:
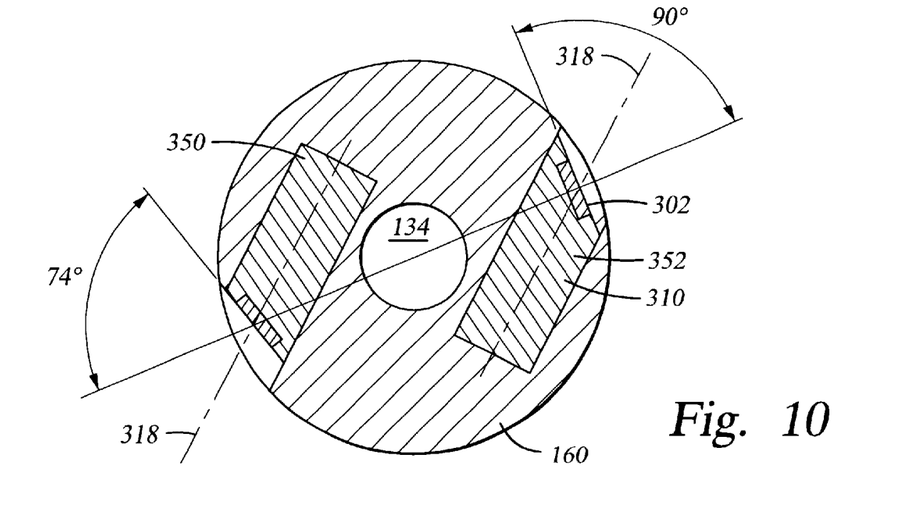
FIG. 10 is a cross-section showing a pair of transducers mounted in an annular shell so as to ring outward.
Figure 11:
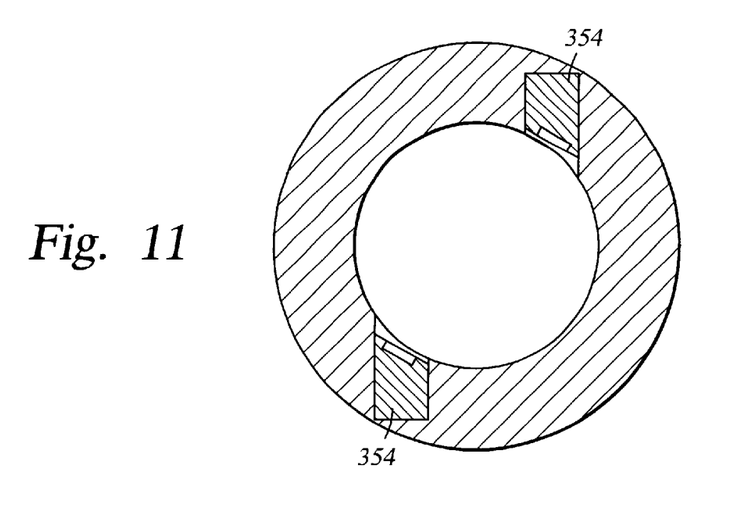
FIG. 11 is a cross-section showing a pair of transducers mounted in an annular shell so as to ring inward.

Regardless of how many transducers are used, it is not necessary that the face of each transducer be perpendicular to a radius of the bore passing through its center point. More specifically, and in contrast to the transducers commonly in use in prior art tools, the longitudinal axis of each transducer (eg. 318 in FIG. 8) does not necessarily lie on a radius of the logging tool, but may be shifted so that it does not intersect the tool axis. It will be understood that this angle can be varied as desired, depending on the desired direction of the transducer radiation pattern. Placing the transducer axis at an angle means that the body of the transducer backing can be made longer than would otherwise be possible. As discussed above, it is desirable to provide as long a backing as possible, so as to maximize attenuation of the backing reverberations that are generated when transducer 302 is fired. For example, in FIG. 10, the face of the left-hand transducer 350 lies at an angle of 74 degrees with respect to a tool radius passing through its center, while the face of the right-hand transducer 352 lies at an angle of 90 degrees with respect to a tool radius passing through its center. Similarly, in FIG. 11, the axis of each transducer 354 lies on an angle with respect to a tool radius through the center of the active (ringing) face. In FIG. 10, transducers 350, 352 face outward from the tool body, while in FIG. 11, transducers 354 face in toward the bore.

Materials

In order to provide an acoustic tool that is capable of surviving downhole for the desired period, the materials from which the various components of the tool are made are selected for long life and compatibility with the other parts of the tool. For instance, fluid components of the tool, such as are used in the pressure balancing system, preferably comprise innert hydrocarbons. Examples of suitable fluids include silicone oil and perfluorinated hydrocarbons, such as that marketed by the 3M corporation under the trademark Fluorinert®.

For the transducers, the backing, piezoelectric material and window are each constructed of conventional materials. Preferred backings are tungsten-loaded epoxies, or tungsten-loaded rubbers. Lead zirconate titanates (PZT) are preferred for the piezoelectric elements and titanium is preferred for the acoustic windows. The PZT is particularly suitable, as it is matched in acoustic impedance to titanium.

Circuitry

A suitable driver circuit for operating the acoustic transmitter of the present invention is any circuitry that provides the piezoelectric transducers with sufficient ringing energy can be substituted. Furthermore, any device capable of generating a detectable acoustic signal in the fluid can be substituted for the transmitting transducers and any device capable of generating a detectable electrical signal in response to the acoustical signal transmitted by the fluid can be substituted for the receiving transducers described below.

Figure 12:
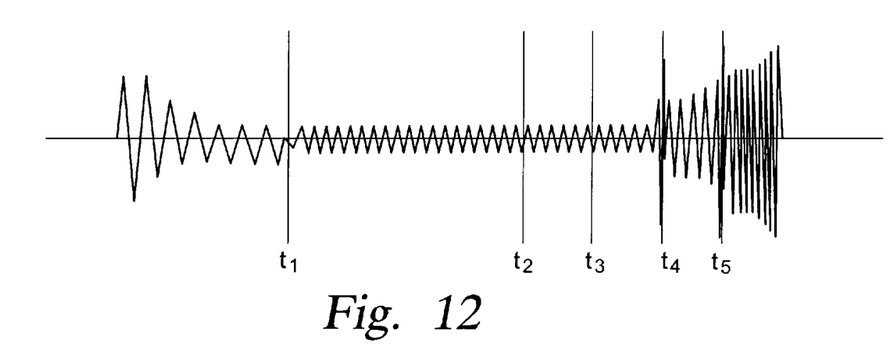
FIG. 12 is a plot of a signal output from a sensor according to the present invention.

Referring briefly to FIG. 12, an exemplary received signal is shown with time periods $t_1$, $t_2$, $t_3$, and $t_4$ marked thereon. In operation, a switch is closed for a time period t defined as $t_1 \leq t \leq t_2$. Time $t_1$ corresponds to the end of the transmitter-induced spurious receiver signal and time $t_2$ corresponds to slightly less than the earliest possible occurrence of a flow-path acoustic signal. Both values are preset, based on calibration of the tool in a controlled environment. During this period, the background noise level is determined by rectification and peak-detection of the filtered acoustic output. This background energy level is stored. The voltage is then multiplied by predetermined multipliers $x_1$ and $x_2$ to give a first threshold THRESHOLD 1 and a second predetermined threshold THRESHOLD 2. Time $t_4$ is defined as the time at which the output from a first comparator indicates that the received signal has exceeded THRESHOLD 1. Similarly, time $t_5$ is defined as the time at which the output from a second comparator indicates that the received signal has exceeded THRESHOLD 2. The two times, $t_4$ and $t_5$, are used to extrapolate back to the time at which the output voltage first became non-zero, i.e. the actual time of the first break $t_b$. For example, using a linear extrapolation, $t_b = t_4 - (t_5 - t_4) = 2t_4 - t_5$. Alternative techniques for determining the first arrival time of the signal transmitted through the fluid are equally acceptable, including setting $t_b = t_4$. In the latter instance, only one level detector is required. Regardless of how $t_b$ is determined, using $t_b$ and the known distance between the transmitter and receiver, the speed of sound for the formation fluid can be calculated.

If it is desired to obtain the real amplitude of the oscillatory signals, the energy envelope of the signal can be determined. The energy envelope is obtained from the equation:

$$A_0 = [(V^2 + (2\pi f) - 2(dV/dt)^2]^{1/2} \qquad (1)$$

where V is the received signal and f is the approximate center frequency of the received signals. This amplitude is measured by full-wave rectification and filtering.

For situations with only one transmitter and one receiver, the attenuation can be estimated by using narrow band electrical filtering to obtain amplitude at several frequencies. The ratios of amplitudes vs. frequencies can be used to estimate the dB per wavelength of attenuation, provided that the frequency dependence of the transducer is relatively constant with time. Stable electronics must be selected. An example of a suitable technique for processing the signal is disclosed in reference to FIG. 5B of U.S. Pat. No. 5,726,951, which is incorporated herein in its entirety.

The optimal frequency range for the present tool depends on the characteristics of the well in which it will be placed and can be determined using known techniques. The preferred tool preferably balances signal strength with accuracy by operating in the range of 50 kHz–200 kHz when the fluids are gaseous and in the range of 100 kHz–2 MHz when the fluids are liquid.

The system described herein provides many advantages over prior art tools, including accurate measurement of inhomogeneous fluids over prolonged periods.

It will be recognized that various modifications can be made in the design and operation of the present invention without departing from the spirit thereof. For example, the transmitters, sensors and signal processing means described herein can be used to advantage in a range of applications, including those such as are described in U.S. Pat. No. 5,841,734, which is incorporated by reference in its entirety. Thus, while the principal preferred construction and mode of operation of the invention have been explained in what is now considered to represent its best embodiments, it should be understood that within the scope of the appended claims the invention may be practiced otherwise than as specifically illustrated and described.

What is claimed is:

1. A tool for measuring a property of a fluid in a pipe, comprising:
    a tool body having a bore aligned with the pipe;
    an acoustic transmitter positioned on one side of said tool body;
    an acoustic receiver positioned opposite said transmitter such that the shortest path between said acoustic transmitter and said acoustic receiver is substantially perpendicular to said bore in said pipe; and
    said tool body being configured to increase the shortest path of an acoustical signal passing from said transmitter to said receiver circumferentially via said tool body without increasing the dimensions of said tool body.

2. The tool according to claim 1 wherein said transmitter and said receiver are substantially flush with said bore in said pipe.

3. The tool according to claim 1 wherein said body, transmitter and receiver are constructed to survive in a downhole environment for at least ten years.

4. The tool according to claim 1 wherein said tool body includes a plurality of cavities that do not include transducers, said cavities positioned to obstruct the transmission of said acoustic signal through said tool body.

5. The tool according to claim 4 wherein said cavities are filled with a signal-damping material.

6. The tool according to claim 1 wherein said tool body comprises an annular inner shell supporting said transmitter and said receiver and an annular outer shell that is acoustically isolated from said transmitter and said receiver, said inner and outer shells being substantially concentric.

7. The tool according to claim 1 wherein said tool body is configured such that the shortest acoustic path through said tool body is longer than one-half the circumference of said tool body, said shortest acoustic path being lengthened by removal of portions of said tool body.

8. The tool according claim 1, further including a hydrostatic pressure balancing system surrounding each transducer, said hydrostatic pressure balancing system designed to protect said transducers from pressure differentials.

9. The tool according claim 8 wherein said hydrostatic pressure balancing system includes a sealed, variable-volume fluid reservoir in fluid communication with said transducer.

10. A method for measuring the speed of sound in a fluid in a pipe, comprising:
    providing a measurement tool having a tool body and having a bore therethrough, said bore in fluid communication with said pipe;
    providing an acoustical transmitter on one side of said tool body;
    providing an acoustic receiver positioned opposite said transmitter such that the shortest path between said acoustic transmitter and said acoustic receiver is substantially perpendicular to said bore in said pipe;
    firing said transmitter so as to produce a signal;

attenuating a first portion of said signal passing from said transmitter to said receiver circumferentially via said tool body by increasing the shortest path of an acoustic signal passing from said transmitter to said receiver circumferentially via said tool body without increasing the dimensions of said tool body; and measuring the transmittal time of said second signal portion.

11. The method according to claim 10, further including the step of passing said second signal portion through a first comparator and determining when a first threshold value is met ($t_1$).

12. The method according to claim 11, further including the step of passing said second signal portion through a second comparator and determining when a second threshold value is met ($t_2$).

13. The method according to claim 12, further including the step of extrapolating a first signal arrival time using $t_1$ and $t_2$.

14. The method according to claim 10, further including the steps of providing a second acoustic transmitter and a second acoustic receiver and using information received from the first and second receivers in a sparse tomographic analysis to yield information about the fluid stream.

15. The method according to claim 10, further including the steps of providing a second acoustic transmitter and a second acoustic receiver and performing a correlation between signals received at the first and second transducers, using the correlation to calculate a time delay, and the time delay to calculate a fluid velocity.

16. A transducer system, comprising:
 a tool body including a bore therethrough, said tool body having an outside diameter and an inside diameter; and
 a transducer member mounted in said tool body, said transducer member comprising a piezoelectric element affixed to a backing, said backing having first and second ends, the distance from said first end to said second end being less than one-half the difference between said outside diameter and said inside diameter.

17. The system according to claim 16 wherein said first backing end is received in said tool body and said piezoelectric element is affixed to said second backing end.

18. The system according to claim 16 wherein said tool body is substantially cylindrical and said bore is axial.

19. The system according to claim 16 wherein said bore is aligned with the bore of a production tubing.

20. An acoustic system for monitoring a property of fluid flowing in a conduit, comprising:
 at least one pair of transducers configured to transmit and receive a signal that traverses a path substantially perpendicular to the direction of flow;
 wherein said pair of transducers comprises an acoustic receiver positioned opposite an acoustic transmitter such that the shortest path between said acoustic transmitter and said acoustic receiver is substantially perpendicular to the direction of flow; and
 wherein said tool body is configured such that the time required for an acoustical signal to pass from said transmitter to said receiver circumferentially via said tool body is greater than the time required for an acoustical signal to pass from said transmitter to said receiver via the fluid, even when the speed of sound in the tool body is faster than the speed of sound in the fluid.

21. The acoustic system according to claim 20, further including a second pair of transducers configured to transmit and receive a signal that traverses a path substantially perpendicular to the direction of flow, said second pair being axially spaced apart from said one pair in a direction parallel to the direction of flow.

* * * * *